(12) United States Patent
Rhyne

(10) Patent No.: US 7,686,806 B2
(45) Date of Patent: Mar. 30, 2010

(54) ANTERIOR CERVICAL PLATE

(75) Inventor: Alfred L. Rhyne, Charlotte, NC (US)

(73) Assignee: Stryker Spine (FR)

( * ) Notice: Subject to any disclaimer, the term of this patent is extended or adjusted under 35 U.S.C. 154(b) by 877 days.

(21) Appl. No.: 11/153,630

(22) Filed: Jun. 15, 2005

(65) Prior Publication Data

US 2006/0287653 A1    Dec. 21, 2006

(51) Int. Cl.
*A61B 17/80* (2006.01)
(52) U.S. Cl. .......................... 606/70; 606/280
(58) Field of Classification Search ............ 606/69–71, 606/280, 250
See application file for complete search history.

(56) References Cited

U.S. PATENT DOCUMENTS

| | | | |
|---|---|---|---|
| D282,580 S | | 2/1986 | Linkow et al. |
| 5,147,360 A | * | 9/1992 | Dubousset .................. 606/250 |
| 5,180,381 A | | 1/1993 | Aust et al. |
| 5,304,210 A | | 4/1994 | Crook |
| 5,330,477 A | | 7/1994 | Crook |
| 5,490,851 A | | 2/1996 | Nenov et al. |
| 5,496,318 A | | 3/1996 | Howland et al. |
| 5,520,690 A | * | 5/1996 | Errico et al. .................. 606/70 |
| 5,603,713 A | * | 2/1997 | Aust et al. .................. 606/279 |
| 5,616,144 A | * | 4/1997 | Yapp et al. .................. 606/280 |
| 5,662,652 A | | 9/1997 | Schafer et al. |
| D402,032 S | | 12/1998 | Stone |
| 5,868,746 A | | 2/1999 | Sarver et al. |
| 5,941,881 A | | 8/1999 | Barnes |
| 5,951,558 A | | 9/1999 | Fiz et al. |
| D420,373 S | | 2/2000 | Bonitz et al. |
| 6,117,135 A | | 9/2000 | Schlapfer et al. |
| 6,129,730 A | | 10/2000 | Bono et al. |
| 6,206,882 B1 | | 3/2001 | Cohen |
| D440,311 S | | 4/2001 | Michelson |
| 6,228,085 B1 | * | 5/2001 | Theken et al. ................ 606/289 |
| 6,261,291 B1 | | 7/2001 | Talaber et al. |
| D449,692 S | | 10/2001 | Michelson |
| 6,336,930 B1 | | 1/2002 | Stalcup et al. |

(Continued)

FOREIGN PATENT DOCUMENTS

EP          1285632 A1 *    2/2003

OTHER PUBLICATIONS

U.S. Appl. No. 29/267,197.

(Continued)

*Primary Examiner*—Eduardo C Robert
*Assistant Examiner*—Julianna N Harvey
(74) *Attorney, Agent, or Firm*—Lerner, David, Littenberg, Krumholz & Mentlik, LLP

(57) ABSTRACT

An anterior cervical plate is adapted to engage at least two vertebrae along the anterior cervical spine. The plate comprises at least one cross connector member connecting two substantially parallel support bars. The anterior surface of the cross connector member is recessed for providing room for the esophagus. The posterior surface of the cross connector member extends slightly into the center of an intervertebral disc space for securing implanted bone graft material, and of course any other suitable intervertebral implant spacer. The preferred configuration of the cross connector member provides torsional resistance for the bone plate. At least two openings are formed in the plate for receiving a fastener therein for fixing the plate to the anterior cervical spine.

19 Claims, 3 Drawing Sheets

U.S. PATENT DOCUMENTS

| | | |
|---|---|---|
| 6,364,880 B1 | 4/2002 | Michelson |
| 6,428,542 B1 | 8/2002 | Michelson |
| 6,547,790 B2 | 4/2003 | Harkey, III et al. |
| 6,592,586 B1 | 7/2003 | Michelson |
| 6,602,255 B1 | 8/2003 | Campbell et al. |
| 6,626,944 B1 | 9/2003 | Taylor et al. |
| D505,205 S | 5/2005 | Freid |
| 6,916,320 B2 | 7/2005 | Michelson |
| 6,945,973 B2 | 9/2005 | Bray |
| 7,001,389 B1 | 2/2006 | Navarro et al. |
| D520,637 S | 5/2006 | Kay et al. |
| 7,052,499 B2 | 5/2006 | Steger et al. |
| 7,060,067 B2 | 6/2006 | Needham et al. |
| 7,074,221 B2 | 7/2006 | Michelson |
| 7,175,624 B2 | 2/2007 | Konieczynski et al. |
| 7,220,263 B2 | 5/2007 | Cordaro |
| 7,229,442 B2 | 6/2007 | Schafer et al. |
| 7,318,825 B2 | 1/2008 | Butler et al. |
| 7,322,984 B2 | 1/2008 | Doubler et al. |
| D574,082 S | 7/2008 | Orthner |
| 2003/0040749 A1 | 2/2003 | Grabowski et al. |
| 2003/0187442 A1* | 10/2003 | Richelsoph et al. ........... 606/70 |
| 2003/0229348 A1* | 12/2003 | Sevrain ....................... 606/70 |
| 2004/0111161 A1* | 6/2004 | Trieu ....................... 623/17.16 |
| 2004/0243239 A1 | 12/2004 | Taylor |
| 2004/0267369 A1 | 12/2004 | Lyons et al. |
| 2005/0004573 A1 | 1/2005 | Abdou |
| 2006/0276795 A1 | 12/2006 | Orbay et al. |

OTHER PUBLICATIONS

U.S. Appl. No. 29/267,173.

* cited by examiner

ANTERIOR CERVICAL PLATE

BACKGROUND OF THE INVENTION

The present invention relates to an anterior cervical plate, and in particular it relates to such a plate with a new and improved H-shaped design.

Anterior cervical plates and their applications are known in the art. Such plates can be attached to the anterior of two or more cervical vertebrae for the purpose of immobilizing, stabilizing, and/or aligning those vertebrae. The plates can be used for a variety of conditions, including for example, providing added strength and rigidity.

The cervical region of the spine is one of the most delicate regions in which to attach a bone plate. The vertebrae of the cervical spine are smaller than the vertebrae located in the thoracic, lumbar, and sacral regions. A spine surgeon who is inserting an anterior cervical plate has exposure to cervical vertebrae C2, down to the cervico-thoracic junction. In this region of the spine, there is less intervertebral disk space between the vertebrae.

An anterior cervical discectomy is the most common surgical procedure to treat damaged intervertebral discs in the delicate cervical region. Anterior access allows the surgeon to remove an entire intervertebral disc, which is not possible during posterior or lateral surgery. Furthermore, spine surgeons often prefer anterior insertion of a bone plate because it provides good access to the spine through a relatively uncomplicated pathway.

The goal of a discectomy is to relieve pressure on nerve roots or on the spinal cord by removing a ruptured intervertebral disc. In this procedure, the cervical spine is reached through a small incision in the front of the neck. During the surgery, the soft tissues of the neck are separated and the disc is removed. In some procedures the resulting space between the vertebrae are left open. However, in order to maintain the normal height of the disc space, the surgeon may choose to fill the space with a bone graft and utilize a plate attached to the anterior faces of the vertebrae. A bone graft can be a small piece of bone, either taken from the patient's body (often the pelvic area) or from a bone bank. This piece of bone fills the disc space and ideally will join or fuse the vertebrae together.

Cervical plates of the present type are generally elongate as to span the distance between two or more vertebrae, as required by a particular application. The plates are generally curved transversely to the spine axis so as to fit the curvature of the vertebrae to which they are attached. Additionally, plates of this type are generally concave longitudinally along the spine axis to match the curvature of the cervical spine.

Cervical plates are provided with openings for receiving bone screws. Typically, cervical plates are secured to adjacent vertebrae by bone screws which pass through openings in the cervical plate. Screw locking systems are provided to keep the vertebral screws from backing out of the plate. In the present invention, each opening in the plate has grooves or recesses for receiving a split ring, though any other suitable screw locking systems may be used. Split rings can be pre-assembled to the bone plate. A split-ring can be sized to expand upon insertion of a bone screw into an opening in the bone plate. Once the head of the screw has passed through the split ring, the split ring can contract under its natural spring tension. When the ring relaxes to its unexpanded state, it prevents the bone screw from backing out of the plate by the engagement of an undersurface of the split-ring and an upwardly facing surface on the bone screw. U.S. Pat. No. 6,602,255, titled "BONE SCREW RETAINING SYSTEM" and issued on Aug. 5, 2003 and U.S. Pat. No. 6,261,291, titled "Orthopedic Implant Assembly" and issued on Jul. 17, 2001, both disclose devices used for securing bone screws to a bone plate and are incorporated herein by reference in their entirety as if fully set forth herein.

Notwithstanding the development of the prior art to date, a need exists for an improved anterior cervical plate having a structure for maintaining or positioning bone graft or other devices in the intervertebral space, providing torsional resistance and avoiding interference with the esophagus.

SUMMARY OF THE INVENTION

A first aspect of the present invention is a bone fixation apparatus. In accordance with this first aspect the bone plate preferably includes support bars and at least one cross connector member configured to connect the support bars. The cross connector member preferably has an anterior surface that is recessed and a posterior surface that is configured to extend into an intervertebral disc space. At least one opening may be formed in each of the support bars for receiving a fastener therein for fixing the bone plate to vertebrae along the anterior cervical spine.

In certain embodiments of this aspect the bone plate may include two cross connector members separated from one another to engage three vertebrae along the anterior cervical spine.

In certain embodiments of this aspect the bone plate may include a generally curved anterior surface.

In certain embodiments of this aspect the anterior surface of the cross connector member is sufficiently recessed to provide room for an esophagus.

In certain embodiments of this aspect the posterior surface of the cross connector member provides torsional resistance for the bone plate.

In certain embodiments of this aspect the fastener is secured to the bone plate by a split ring.

In certain embodiments of this aspect the first and second supports bars are substantially parallel and are symmetrical about a longitudinal axis of the bone plate.

Another aspect of the present invention is another bone fixation apparatus. In accordance with this aspect the bone plate preferably includes at least one cross connector member configured to connect the support bars. The cross connector member preferabaly has a posterior surface that is configured to extend into an intervertebral disc space. At least one opening may be formed in each of the support bars for receiving a fastener therein for fixing the bone plate to vertebrae along the anterior cervical spine.

Another aspect of the present invention is a method of securing a bone fixation apparatus to at least two vertebrae separated by an intervertebral disk space along the anterior cervical spine. The method preferably includes the steps of placing a bone plate having a pair of generally parallel support bars connected by a cross connector against at least two vertebrae along the anterior cervical spine, inserting an extension in the posterior surface of the cross connector member into the intervertebral disk space, affixing a first support bar on the left side of the mid-line of the spine to a vertebra along the cervical spine by applying a fastener, affixing a second support bar on the right side of the mid-line of the spine to a vertebra along the cervical spine by applying a fastener, and allowing the esophagus to be disposed in a concave recessed area extending across said bridge and into each of said support bars.

Yet another aspect of the present invention is an anterior cervical fixation plate. In accordance with this aspect the bone plate preferably includes spaced first and second elongate bar members having anterior and posterior surfaces and first and second ends. At least one bridge preferably connects the spaced first and second bar members. The bridge may be located between the first and second ends of the elongate members. The bridge preferably has an anterior surface bar with a depression therein extending across the bridge into the anterior surface of the first and second bar members. The bridge may also have a posterior surface extending beyond at least a portion of the posterior surface of the first and second members.

In certain embodiments of this aspect the anterior surface of the first and second members is convex except in the area of the depression in the bridge. The depression in the bridge preferably has a concave surface.

In certain embodiments of this aspect the posterior surface of the first and second elongate bar members is concave except in the area of the bridge posterior surface. The posterior surface of the bridge may be substantially flat.

In certain embodiments of this aspect the bone plate may include a pair of bridge elements intermediate the first and second ends of the elongate members.

In certain embodiments of this aspect the depression is of sufficient depth to provide space for an esophagus and the first and second members are generally parallel.

In certain embodiments of this aspect the concave posterior surface and the convex anterior surface of the first and second bar members may have an arcuate component extending in the elongate direction between the first and second ends and an arcuate component extending in a direction generally perpendicular thereto.

In accordance with another aspect of the invention, a plate for anterior fixation of vertebrae includes a support bar positioned on the left and right side of the mid-line of the spine and at least one cross connector or bridge member extending laterally between the support bars for positioning in the area of an intervertebral disc space from an anterior-posterior view. Additionally, the plate is sufficient in length to span at least two vertebrae with the plate including one or more openings shaped to accept the head of a mating fastener such as a bone screw.

For the purpose of securing bone graft material, and of course any other suitable intervertebral implant spacer, after fusion of adjacent vertebrae, a cross connector member extends slightly into the anterior portion of an intervetebral disc space. The portion of the cross connector member which extends slightly into the space acts as a buttress for the fused bone graft material. Movement of the spine in any direction after surgery can loosen the fused bone graft material and the preferred embodiment counteracts such movement.

In accordance with another aspect of the present invention, each cross connector member included in the plate extends slightly into an intervetebral disc space for the purpose of torsional resistance. A preferred anterior cervical bone plate is curved transversely so as to fit the curvature of the vertebrae to which it is attached and concave longitudinally thereof to match the curvature of the cervical spine. Having the cross connector member extend into the disc space allows the member to have sufficient thickness to resist rotational movement while still exhibiting the above mentioned configuration of a preferred bone plate. After surgery, almost every movement of the body creates movement of the spinal axis creating bending moments. Each successive moment created is an event in which bone graft material could be dislodged. The present embodiment counteracts the affects of such moments.

In yet another aspect of the present invention, each cross connector member included in the plate has an anterior surface which is recessed posteriorly of the support bars in order to provide room for the esophagus. After the plate is affixed to the vertebrae of the spine, the esophagus can rest against the plate. The esophagus can rest without resistance, if the cross connector member of the plate it can rest against is recessed posteriorly of the support bars. The present invention provides sufficient room for the esophagus.

These and other objects of the present invention will be apparent from the detailed description to follow, together with the accompanying drawings.

BRIEF DESCRIPTION OF THE DRAWINGS

There follows a detailed description of preferred embodiments of the present invention which are to be read together with the drawings therein.

DETAILED DESCRIPTION

Figure 1:
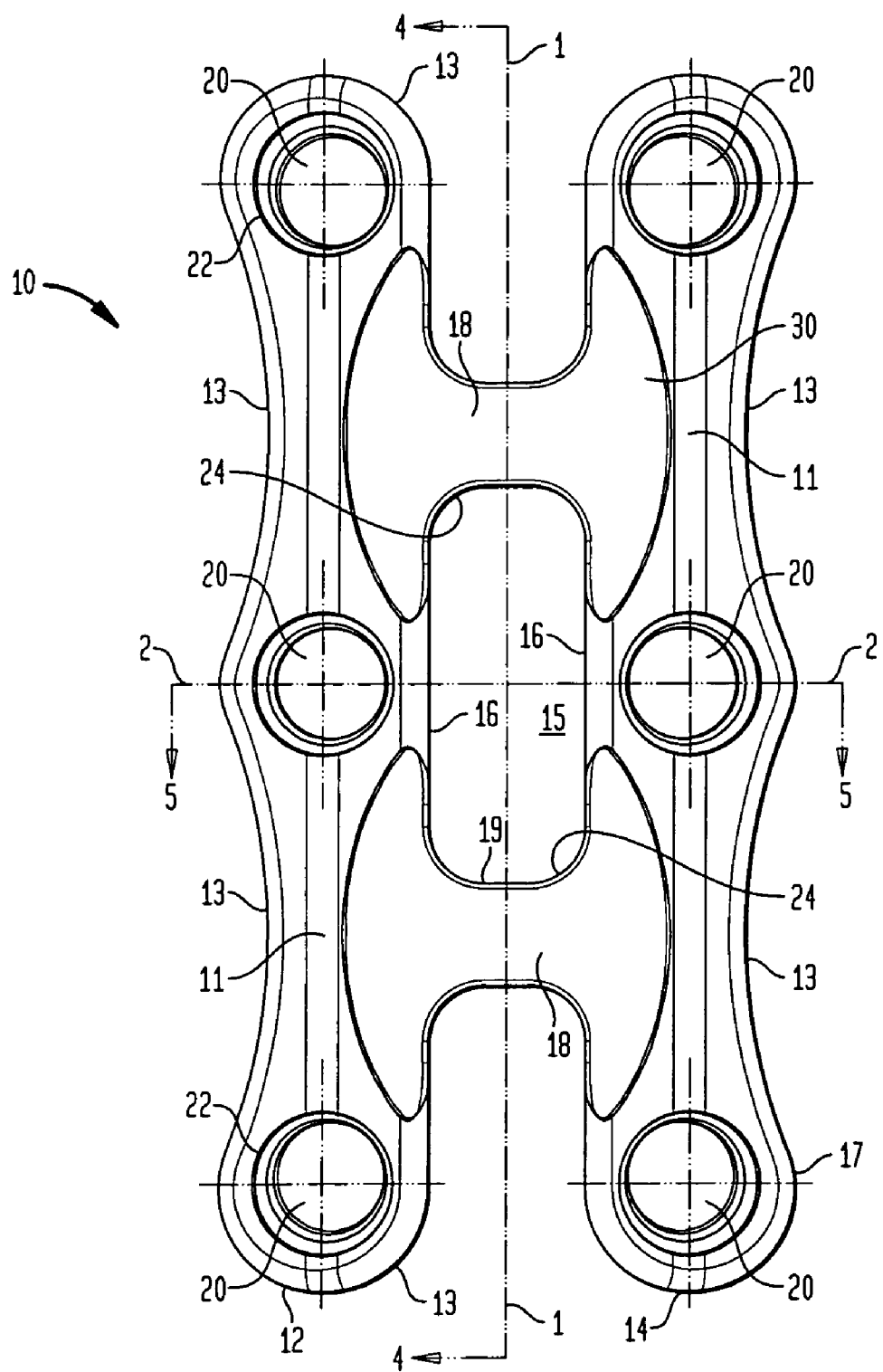
FIG. 1 is a top plan view of an anterior cervical plate in accordance with the present invention.

The preferred embodiment of the present invention shown in FIGS. 1-5 is directed to an improved H-shaped anterior cervical plate. Referring now to the drawings, FIGS. 1-5 illustrate a bone plate made in accordance with the principles of the present invention, and more particularly an improved H-shaped anterior cervical bone plate design generally denoted as 10. The bone plate 10 may be manufactured from any suitable biocompatible material, including titanium, titanium alloy, stainless steel, cobalt chrome alloys or even resorbable materials. The bone plate 10 has a pair of support bars 12 and 14 each having an anterior surface 11 and side an outer edge generally curved at 13.

In FIG. 1, the preferred bone plate 10 is illustrated as having a longitudinal axis 1. Longitudinal axis 1, when implanted, aligns with the mid-line of the anterior cervical spine and acts as an axis of symmetry for bone plate 10. In preferred bone plate 10 first support bar 12 and second support bar 14 are equidistant on each side of longitudinal axis 1. Since the plate 10 is symmetrical, first support bar 12 may be positioned on the right or left side of the mid-line of the spine and likewise second support bar 14 may be positioned on the right or left side of the mid-line of the spine.

In the preferred embodiment, support bars 12 and 14 extend parallel to one another and are spaced to form openings 15 therebetween. Preferably support bars 12 and 14 include facing edge surfaces 16 forming sides of the opening 15. Each cross bar 12, 14 preferably include three apertures 20 for receiving bone screws (not shown). Preferably, the bone screw openings are located at first and second ends of each support bar as well as along central axis 2 of plate 10. Axis 2 also forms an axis of symmetry thus allowing the plate to be implanted in either orientation. The outside edge 17 of each of the first and second ends of support bars 12 and 14 preferably has a radius of about 4 mm.

In the preferred embodiment, bone plate 10 comprises two cross connector or bridge members 18 which define opening 15. Preferred bone plate 10 engages three vertebrae along the anterior cervical spine. The plate is sized so that each cross connector member 18 is positioned in the center of an intervertebral disc space. While two cross connectors are shown in FIG. 1, a single cross connector could be used if plate 10 is intended to span two vertebrae. Cross connector members 18 connect first support bar 12 and second support bar 14. Opening 15 has a curved portion 24 acting as a transition between edge 16 and the horizontal portion 19 of the cross connector member 18 which is perpendicular to the substantially flat edge portion 16 of the support bars 12, 14. In the preferred embodiment, the curved portion 24 has a radius of about 2 mm. The entire anterior surface 11 of preferred bone plate 10 is generally convexly curved to be consistent with the bone, for instance to be consistent with the anterior vertebral surface of the bone.

As indicated above, in another embodiment, bone plate 10 may comprise only one cross connector member 18 and engages two vertebrae along the anterior cervical spine. In yet another embodiment, bone plate 10 may comprise three cross connector members 18 and engages four vertebrae along the anterior cervical spine.

Bone plate 10 comprises at least a pair of apertures 20 with at least one formed in first support bar 12 and one in second support bar 14 for receiving a fastener therein and fixing the bone plate 10 to vertebra along the anterior cervical spine. A circumferential chamfered edge 22 may surround plate openings 20 and tapers to the diameter of the plate openings 20 which receive fasteners therein.

Figure 2:
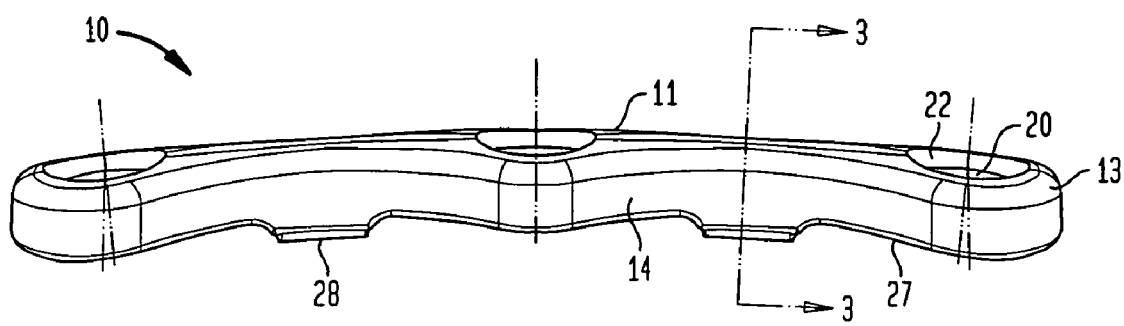
FIG. 2 is a side elevation view of FIG. 1.
Figure 5:
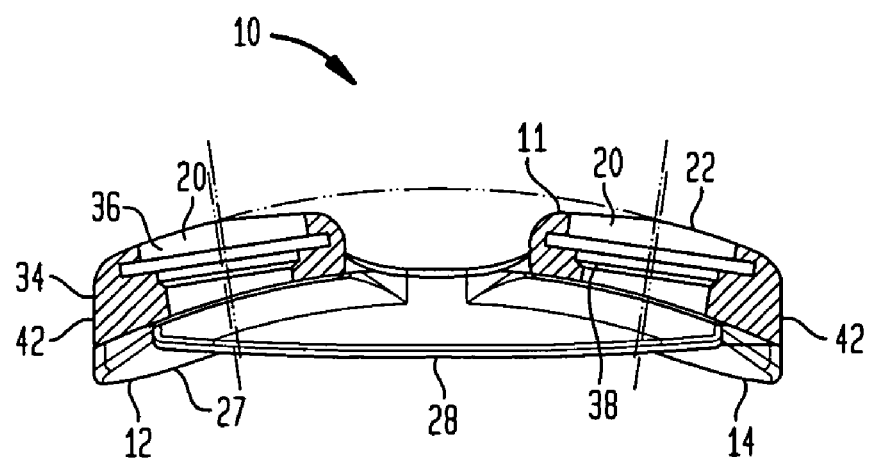
FIG. 5 is a cross sectional view taken along line 5-5 of FIG. 1.

Referring to FIGS. 2 and 5, preferred posterior surface 27 of bone plate 10 is shown to be generally curved transversely so as to fit the curvature of the vertebrae to which they are attached. Additionally, surface 27 of preferred bone plate 10 is concave longitudinally thereof to match the curvature of the cervical spine.

Figure 3:
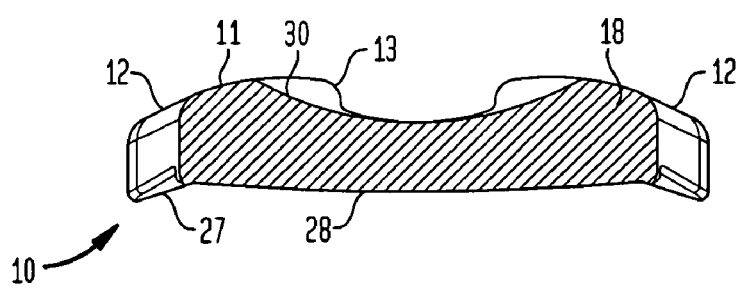
FIG. 3 is a cross sectional view taken along line 3-3 of FIG. 2.

FIG. 3, is an illustration of a cross sectional view taken through cross connector 18 along line 3-3 of FIG. 2. Cross connector member 18 has a posterior surface 28 that protrudes beyond at least the adjacent portion of the support bars to extend into an intervertebral disc space of the anterior cervical spine.

The anterior surface of cross connector member 18 also comprises a preferably concave recessed portion 30 that has a radius of about 12.5 mm. Recessed portion 30 of cross connector member 18 is recessed posteriorly into at least part of first support bar 12 and second support bar 14. In the preferred embodiment, the recess in bars 12 and 14 extend about halfway through their width and ends adjacent holes 20 therein. After the bone plate 10 is affixed to the vertebrae of the spine, the esophagus has room in the area of or may rest against the recessed portion 30 of the cross connector member 18. In the preferred embodiment, the esophagus has room in the area of or may rest on the recessed portion 30 of the cross connector member 18 without interference. The preferred embodiment therefore provides sufficient room for the esophagus.

It is noted that in the middle 6 mm of the anterior cervical spine, there is less than 1.5 mm, perhaps about 1 mm, of distance between the esophagus and anterior face of the vertebral bodies. Accordingly, the thickness of the plate and the recessed portion 30 can be made accordingly to provide room for the esophagus.

Also illustrated in this view is the anterior surface 11 of the bone plate 10 which has sides that are generally curved at 13. The generally curved sides 13 of the bone plate 10 accommodate surrounding body parts of the anterior cervical spine. As shown in FIG. 2, a preferred anterior cervical bone plate is curved transversely along axis 2 so as to fit the curvature of the vertebrae to which it is attached and concave longitudinally along axis 1 thereof to match the curvature of the cervical spine. Thus, anterior surface 11 is transversely convexly curved and posterior surface 27 is concavely transversely curved as well as being curved in the longitudinal direction so that there are curved components in two directions.

Figure 4:
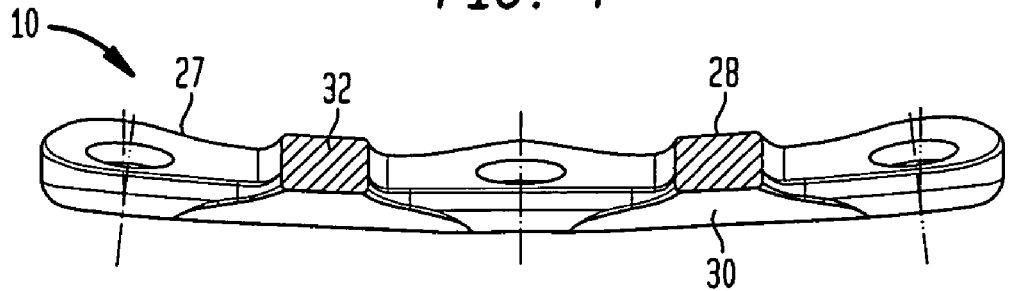
FIG. 4 is a cross sectional view taken along line 4-4 of FIG. 1.

FIG. 4, is an illustration of a cross sectional view taken along line 4-4 of FIG. 1. The preferred cross connector member 18 has a protruding portion with a generally rectangular cross-section 32 along the mid-line of the spine. The generally rectangular 32 protruding portion of the cross connector member provides the bone plate 10 with additional torsional resistance due to its larger cross-section. Having the posterior of cross connector member 18 extend into an intervertebral disc space allows the member 18 to have sufficient thickness to also resist rotational movement while still exhibiting the configuration of the preferred bone plate. The posterior surface 28 of the cross connector member extends into the disc space and acts as a buttress for the fused bone graft material. Movement of the spine in any direction after surgery can loosen the bone graft material and the preferred embodiment counteracts the affects of such movement.

FIG. 5, is a cross sectional view taken along line 5-5 of FIG. 1. In FIG. 5, a cross section of the plate openings 20 which can receive a fastener (not shown), such as a bone screw, therein are illustrated. Circumferential chamfered edge 22 of plate openings 20 are located on anterior surface 11 of bone plate 10. A split ring can rest on surface 34 inside a groove defined by surface 34 and surface 36 of the plate opening 20. The split-ring is sized to expand upon insertion of a bone screw into plate opening 20. Once the head of the screw has passed through the split ring, the split ring can contract under its natural spring tension. After passing through the split ring, the ring relaxes to its unexpanded state and prevents the bone screw from backing out of plate 10 by the engagement of an undersurface of the split-ring and an upwardly facing surface on the bone screw. The bone screw rests secured on a ledge surface 38 of the plate opening 20. U.S. Pat. No. 6,602,255 titled "BONE SCREW RETAINING SYSTEM" is a device used for securing bone screws to a bone plate and is herein incorporated by reference in its entirety in the present application. Of course other methods can be used to insure the vertebral screws do not back out of holes 20.

Referring to FIG. 5 in the preferred embodiment, the radius of the anterior surface 11 of the support bars 12, 14 is about 75 mm. A curved corner portion 40 acts as a transition from the anterior surface 11 of the support bars 12, 14 to the side portions 42 of the support bars 12, 14. The curved portion 40 has a radius of about 1 mm. the plate should be as thin as possible while maintaining the requisite strength for stabilization.

Although the invention herein has been described with reference to particular embodiments, it is to be understood that these embodiments are merely illustrative of the principles and applications of the present invention. It is therefore to be understood that numerous modifications may be made, and are encouraged to be made, to the illustrative embodiments and that other arrangements may be devised without departing from the spirit and scope of the present invention as defined by the appended claims.

The invention claimed is:

1. A bone fixation apparatus for engaging at least first and second vertebrae, comprising:
   a bone plate having a first support bar and a second support bar,
   at least one cross connector member connecting the first support bar and second support bar, the cross connector member having an anterior surface and a posterior portion, the anterior surface being recessed at least between the first and second support bars and at least a part of the posterior portion being configured to extend into an intervertebral disc space; and at least first and second openings formed in the first support bar and at least third and fourth openings formed in the second support bar, the first and third openings for receiving fasteners therein for fixing the bone plate to the first vertebrae along the anterior cervical spine and the second and fourth openings for receiving fasteners therein for fixing the bone plate to the second vertebra along the anterior cervical spine, wherein the bone fixation apparatus prevents movement between the first and second vertebrae, and the anterior surface of the cross connector member is sufficiently recessed to provide room for an esophagus.

2. The bone fixation apparatus of claim 1, further comprising two cross connector members separated from one another.

3. The bone fixation apparatus of claim 2, wherein the bone plate is configured to engage first, second, and third vertebrae along the anterior cervical spine.

4. The bone fixation apparatus of claim 3, further including a fifth opening formed in the first support bar for receiving a fastener therein for fixing the bone plate to the third vertebra along the anterior cervical spine and a sixth opening formed in the second support bar for receiving a fastener therein for fixing the bone plate to the third vertebra along the anterior cervical spine.

5. The bone fixation apparatus of claim 1, wherein the bone plate has a generally curved anterior surface.

6. The bone fixation apparatus of claim 1, wherein the part of the posterior portion of the cross connector member provides torsional resistance for the bone plate.

7. The bone fixation apparatus of claim 1, wherein the first and second support bars are symmetrical about a longitudinal axis of the bone plate.

8. The bone fixation apparatus of claim 1, wherein the first support bar and second support bar are substantially parallel.

9. A bone fixation apparatus for engaging at least first and second vertebrae, comprising:

a bone plate having a first support bar and a second support bar;

at least one non-apertured cross connector member connecting the first support bar and second support bar, the cross connector member having an anterior surface and a posterior portion, the anterior surface being recessed at least between the first and second support bars and at least a part of the posterior portion being configured to extend into an intervertebral disc space; and at least first and second openings formed in the first support bar and at least third and fourth openings formed in the second support bar, the first and third openings for receiving fasteners therein for fixing the bone plate to the first vertebrae and the second and fourth openings for receiving fasteners therein for fixing the bone plate to the second vertebra, wherein the bone fixation apparatus prevents movement between the first and second vertebrae, and the anterior surface of the cross connector member is sufficiently recessed to provide room for an esophagus.

10. An anterior cervical fixation plate for engaging at least first and second vertebrae comprising:

spaced first and second elongate bar members having anterior and posterior surfaces and first and second ends;

at least one bridge integrally formed with and connecting the spaced first and second bar members, the bridge located between the first and second ends of the elongate members, the at least one bridge having an anterior surface with a depression extending across the bridge into the anterior surface of the first and second bar members and the at least one bridge having a posterior portion at least a part of which extends beyond at least a portion of the posterior surface of the first and second members; and at least first and second openings formed in the first bar member for receiving fasteners therein for fixing the plate to the first and second vertebrae and at least third and fourth openings formed in the second bar member for receiving fasteners therein for fixing the plate to the first and second vertebrae, wherein the depression is of sufficient depth to provide space for an esophagus.

11. The anterior cervical fixation plate as set forth in claim 10, wherein the anterior surface of the first and second members is convex except in the area of the depression in the bridge.

12. The anterior cervical fixation plate as set forth in claim 11, wherein the depression has a concave surface.

13. The anterior cervical fixation plate as set forth in claim 11, wherein the posterior surface of the first and second elongate bar members is concave except in the area of the bridge posterior surface.

14. The anterior cervical fixation plate as set forth in claim 13, wherein the posterior surface of the bridge is substantially flat.

15. The anterior cervical fixation plate as set forth in claim 13, wherein the concave posterior surface and the convex anterior surface of the first and second bar members have an arcuate component extending in the elongate direction between the first and second ends and an arcuate component extending in a direction generally perpendicular thereto.

16. The anterior cervical fixation plate as set forth in claim 10, wherein the posterior surface of the first and second elongate members is concave except in the area of the bridge posterior surface.

17. The anterior cervical fixation plate as set forth in claim 10, wherein the posterior surface of the bridge is substantially flat.

18. The anterior cervical fixation plate as set forth in claim 10, comprising a pair of bridge elements intermediate the first and second ends of the elongate members.

19. The anterior cervical fixation plate as set forth in claim 10, wherein the first and second members are generally parallel.

* * * * *